(12) United States Patent
Barbour

(10) Patent No.: US 6,937,884 B1
(45) Date of Patent: Aug. 30, 2005

(54) METHOD AND SYSTEM FOR IMAGING THE DYNAMICS OF SCATTERING MEDIUM

(75) Inventor: Randall L. Barbour, Glen Head, NY (US)

(73) Assignee: The Research Foundation of State University of New York, Albany, NY (US)

( * ) Notice: Subject to any disclaimer, the term of this patent is extended or adjusted under 35 U.S.C. 154(b) by 157 days.

(21) Appl. No.: 10/088,190

(22) PCT Filed: Sep. 14, 2000

(86) PCT No.: PCT/US00/25136

§ 371 (c)(1),
(2), (4) Date: Mar. 14, 2002

(87) PCT Pub. No.: WO01/20305

PCT Pub. Date: Mar. 22, 2001

Related U.S. Application Data

(60) Provisional application No. 60/154,099, filed on Sep. 15, 1999, provisional application No. 60/153,926, filed on Sep. 14, 1999.

(51) Int. Cl.$^7$ .............................................. A61B 6/00
(52) U.S. Cl. ...................... 600/473; 600/407; 600/476; 600/310; 600/323; 356/39; 356/40; 356/41; 382/128; 382/130; 250/353.04
(58) Field of Search .................. 250/353.04; 600/473, 600/476, 310, 323; 356/39, 40, 41; 382/128, 382/130

(56) References Cited

U.S. PATENT DOCUMENTS

| | | | |
|---|---|---|---|
| 5,291,886 A * | 3/1994 | Katayama et al. .......... 600/310 |
| 5,994,690 A | 11/1999 | Kulkarni et al. |
| 6,006,128 A * | 12/1999 | Izatt et al. .................. 600/476 |
| 6,263,227 B1 * | 7/2001 | Boggett et al. ............. 600/407 |
| 6,335,792 B1 * | 1/2002 | Tsuchiya .................... 356/432 |
| 2003/0135122 A1 * | 7/2003 | Bambot et al. ............. 600/476 |

* cited by examiner

*Primary Examiner*—Brian L. Casler
*Assistant Examiner*—William C Jung
(74) *Attorney, Agent, or Firm*—Scully, Scott, Murphy & Presser

(57) ABSTRACT

A method and system for imaging the dynamics of a scattering medium (116) is provided. The method and system generates contrast and resolution enhanced images of dynamic properties of a medium having a temporal signature by using time series analysis methods on a time series of collected data or time series of images to extract and isolate dynamic properties of the medium (116).

24 Claims, 18 Drawing Sheets

METHOD AND SYSTEM FOR IMAGING THE DYNAMICS OF SCATTERING MEDIUM

This application claims the benefit under 35 U.S.C. §120 of prior U.S. Provisional Patent Application Ser. No. 60/153,926 filed Sep. 14, 1999, entitled DYNAMIC TOMOGRAPHY IN A SCATTERING MEDIUM and 60/154,099 filed Sep. 15, 1999, entitled DYNAMIC TOMOGRAPHY IN A SCATTERING MEDIUM.

This application is related to copending application Ser. No. PCT/US00/25155, filed on the same date as this application, entitled "SYSTEM AND METHOD FOR TOMOGRAPHIC IMAGING OF DYNAMIC PROPERTIES OF A SCATTERING MEDIUM" by inventors R. Barbour and C. Schmitz and is hereby incorporated by reference (hereinafter the "Barbour 4147PC1 application"). The counterpart U.S. patent application is application Ser. No. 10/088,254 filed Mar. 14, 2002.

This application is also related to copending application Ser. No. PCT/US00/25156, filed on the same date as this application, entitled "IMAGING OF SCATTERING MEDIA USING RELATIVE DETECTOR VALUES" by inventor R. Barbour and is hereby incorporated by reference (hereinafter the "Barbour 4149PC2 application"). The counterpart U.S. patent application is application Ser. No. 10/088,192, filed Mar. 14, 2002.

This invention was made with U.S. Government support under contract number CA-RO166184-02A, awarded by the National Cancer Institute. The U.S. Government has certain rights in the invention.

FIELD OF THE INVENTION

The invention relates to the field of imaging in a scattering medium, and in particular to methods of imaging the dynamics of a scattering medium.

BACKGROUND

Imaging in a scattering medium relates generally to the methods and techniques for generating an image of the internal properties of a scattering medium based on the detection of scattered energy.

Many systems and techniques have been developed for imaging of scattering media. A typical system for imaging based on scattered energy detection includes a source for directing energy into a target medium and a plurality of detectors for measuring the scattered energy exiting the target medium at various locations with respect to the source. Based on the measured energy exiting the target medium, it is possible to reconstruct an image representation of the cross-sectional scattering, absorption or other properties of the target medium. The values of the absorption and scattering properties of the medium can vary depending on the wavelength and types of energy employed as an imaging source. These values are also frequently spatially varying. These techniques permit the use of types of energy and wavelengths, such as near infrared light energy, that are not suitable for projection imaging techniques, such as x-ray imaging. Thus these techniques have great potential for detecting and imaging properties of media, such as human tissue, that can not be revealed using energy sources commonly employed in projection imaging methods.

Exemplary methods and systems for imaging of scattering media are disclosed in Barbour et al., U.S. Pat. No. 5,137,355, entitled "Method of Imaging a Random Medium," (hereinafter the "Barbour '355 patent"), Barbour, U.S. Pat. No. 6,081,322, entitled "NIR Clinical Opti-Scan System," (hereinafter the "Barbour '322 patent"), the Barbour 4147PC1 application, the Barbour 4149PC1 application and the Barbour 4147PC2 application.

As can readily be appreciated, there are many instances where use of these techniques are highly desirable. For example, one flourishing application area is in the field of optical tomography. Optical tomography typically uses near infrared (NIR) energy as an imaging source. Contrary to imaging methods relying on the use of ionizing radiation and/or toxic/radioactive contrast agents, NIR optical tomographic imaging methods bear no risk of causing harm to the patient. The dose of optical intensity used remains far below the threshold of thermal damage and is therefore safe. In the regime of wavelength/intensity/power used, there are no effects on the tissue that accumulate with increasing light energy dose due to over-all irradiation time.

Other favorable attributes of optical tomography include the use of low-cost, potentially portable devices that employ highly integrated, economical off-the-shelf data processing electronics and semiconductor lasers (laser diodes). Such features contrast with other imaging technologies commonly used in clinical diagnosis that require large, fixed facilities such as MRI and x-ray CT imaging. Additionally, since a significant computational effort may be required for both image reconstruction and data analysis, the technology particularly gains from the exponential growth in the ratio of computing power to cost.

It is well appreciated that optical tomography has the potential to provide insights into anatomy and physiology that are unavailable from other imaging methods. For example, optical tomography, using near infrared energy, can identify the spatial variations in blood volume and blood oxygenation levels because of its sensitivity to hemoglobin states. These measures have considerable potential value in diagnosing a broad range of disease processes that are known to influence hemoglobin states.

For example, a common feature of breast tumors, and solid tumors generally, is the occurrence of neovascularized tissue. Ultrastructurally, these tissues are highly disorganized and exhibit functional abnormalities. Often the microvessels are dilated, tortuous, elongated and saccular. There is excessive branching of the vessels, including significant arterio-venous shunting as well as blind vascular endings. Aberrant vascular morphology and decreased vessel density are responsible for increase resistance to flow. The resistance to flow combined with an enlarged diffusion distance, due to the expansion of the extravascular space, can lead to perfusion with hypoxemic and nutrient-deprived blood. The net effect of this state is the occurrence of substantial spatial and temporal heterogeneity in the tumor metabolic microenvironment.

Although these attributes of disease tissue are well appreciated, the availability of a suitable detection methodology able to take full advantage of these characteristics has been notably lacking. An appropriate methodology would be one sensitive not only to altered hemoglobin states (i.e., localized variations in tissue blood volume and oxygenation states), but also to their dynamics under homeostatic conditions or in response to specific provocations.

A variety of methods involving imaging and non-imaging modalities are available for assessing specific features of the vasculature. Detailed images of the vascular architecture involving larger vessels (>1 mm dia.) can be provided using x-ray enhanced contrast imaging or MR angiography. These methods however are insensitive to hemoglobin states and only indirectly provide measures of altered blood flow. The latter is well accomplished, in the case of larger vessels, using Doppler ultrasound, and for near-surface microvessels by laser Doppler measurements, but each is insensitive to variations in tissue blood volume or blood oxygenation. Ultrasound measurements are also limited by their inability to penetrate bone.

In principle, imaging methods based on the detection and analysis of scattered energy, such as optical tomograpic methods, can provide either direct or indirect measures of all of these parameters. However, the known methods and systems have several shortcomings. First, known methods and systems provide images having low contrast and resolution. Second, these methods and systems do not image the dynamic properties of highly scattering media. Third, these methods and systems require accurate calibration and are susceptible to errors. There are several reasons for these problems with known systems and methods. These reasons relate principally to how measurements are performed and how measurement data is analyzed.

For example, when imaging human tissue, the natural occurrence of vascular frequencies arising from cardiac, respiratory and vasomotor activity, produces time variations in, for example, the absorption properties of tissue due to changes in tissue blood volume. Significantly, the process of vasomotion, perfusion first in one region, then another, can be expected to produce spatially convolved images should data be collected on a time frame that is long compared to the reciprocal of the frequency of these processes. Thus methods that collect time-averaged data will predictably yield images whose contrast and resolution are degraded by such variability.

Also influencing the quality of reconstructed images, is the approach used to analyze the acquired data. Many of the known imaging schemes consider, in some manner, the comparison of measured values to predicted values. Typically, these methods, including that described in the Barbour '355 patent, employ numerical methods that seek to minimize the difference between sets of measured and predicted values, and in doing so seek to provide improved estimates of the properties of the unknown target medium. These analysis schemes, referred to as model based methods, assume equivalency in the efficiency of measured detector values and computed predicted values. Although the derivation of accurate estimates of the efficiency of measured responses is possible in principle, in practice, the natural plasticity of tissue, its mainly arbitrary shape and variable composition and noted variability in hemoglobin levels, all serve to confound efforts to devise practical methods that provide reliable estimates.

In addition, the physics of light transport in highly scattering media, such as tissue, imposes further practical constraints that relate to the method adopted for data analysis. At issue is the required accuracy of assumptions made in order to generate predicted detector values, especially those adopted for the initial estimate. These assumptions are commonly referred to as the "initial guess". Small errors in the initial guess of optical properties of the reference medium can lead to large errors in the computed detector values. One consequence of this can be the severe corruption of the information content of the data vectors leading to artifact-laden images. Adding to the mentioned uncertainties is the well-known property of reconstruction methods that employ linear operators regarding their sensitivity to undetermined data sets (i.e., insufficient amount of collected data) and measurements based on restricted views (e.g., backscatter only, transmission only). The net effect of these limitations can render solutions to image recovery problems of this type overly sensitive to the influence of experimental noise (i.e., ill-conditioned), provide nonunique solutions (ill-posed) or both.

These concerns are well appreciated by those skilled in the art of image reconstruction methods. It is also well appreciated that, in general, there are no simple or well-defined methods that can be universally applied to overcome the noted limitations. In this regard, specification of suitable conditions that can satisfactorily deal with the noted concerns is an art whose successful implementation requires considerable skill.

In addition to the need to provide stable solutions to the image reconstruction problem, consideration of the information content of the reconstructed image has considerable importance. As presently practiced, the method of optical tomography considers the evaluation of static states or employs time averaging methods to minimize the influence of signal instability originating from tissue dynamics.

The goal of these studies is to provide image maps that define spatial variations in the optical properties of tissue (usually, absorption and scatter) from which may be derived, for instance, estimates of spatial varying hemoglobin states. It is understood however, that the latter is fundamentally governed by dynamic processes whose details have the potential to reveal a wealth of information regarding functional features of the vasculature, in particular as it relates to its interaction with surrounding tissue.

The ability to measure dynamic processes of a medium can reveal information that is unobservable from static or time-averaged measures. In the case of physiological systems, the form of the dynamic process has added significance. For instance, it is well understood that many time varying processing have an underlying nonlinear character. Nonlinear dynamic processes, in biological systems, are often chaotic and exhibit the characteristic feature of sensitivity to initial conditions.

The existence of such behavior has important implications in the understanding of disease processes and well as for the approaches taken for therapy. For instance, the approach needed to control a chaotic system is quite different from that for a linear system, wherein the system response is proportional to the magnitude of the input stimulus. Thus it has been proposed that more effective therapies can be realized from a series of well-timed perturbations rather than from the standard approach of applying a constant stimulus, the method commonly used in many pharmacological interventions. Also of interest, and related to this, is the seemingly general finding that the occurrence of chaotic behavior in physiological systems is a sign of health and its absence is a sign of disease.

For instance, it is known that heart rate variability is chaotic. Significantly, loss of this signature with the appearance of periodic oscillations is among the strongest predictors of sudden cardiac death. A similar phenomenology has been observed in infants who succumb to sudden infant death syndrome. In this case, the normally chaotic respiratory rate becomes periodic prior to the fatal incident. Similarly, during epileptic seizures, electroencephalographic recordings exhibit a transition from chaotic to periodic activity.

Presently, the capacity to monitor dynamic behavior in vascular structures is limited principally to near surface measures using laser Doppler methods. Measures of the time variability of the vascular caliber and flow motion for larger vessels is possible using Duplex ultrasound. However, these measures are insensitive to the activity of the microvasculature, do not provide for full cross-sectional views, and are not sensitive to the dynamics of hemoglobin states.

Although optical methods, such as Laser Doppler, pulse oximetry, photoplethysmography and the like, can be used to monitor dynamic states of the vasulature, none are capable of providing such measures in the form of a cross-sectional image, especially in the case of large tissue structures. Moreover, known optical methods for cross-sectional imaging of the properties of a scattering media have not been used to derive dynamic measures of these states, and are plagued with a host of technical limitations, such as low contrast, low resolution images, prolonged computing times, excessive sensitivity to errors in initial estimates. These limitations render it unlikely that useful information regarding dynamic states could be derived from these known methods.

Overcoming the indicated drawbacks and concerns is critical for widespread practical implementation of optical tomography as a diagnostic tool because (1) improved contrast and resolution are essential to feature identification and visualization, (2) a static (snapshot) or time averaged image of a time evolving property does not provide discovery of the physiological dynamic processes and (3) measures of dynamic processes can yield critical information needed for improved diagnostic methods and therapies.

For the foregoing reasons, there is a need for a method of improving the contrast and resolution of reconstructed images. There is also a need for a method of imaging dynamic properties of dense scattering media, especially as it relates to dynamic properties of vascular states in large tissue structures as revealed by time variation in hemoglobin states. There is yet a further need for a method that can provide dynamic images without undue reliance on complex calibration schemes or computationally intensive numerical methods.

SUMMARY OF THE INVENTION

The present invention satisfies these needs by providing a method for (1) enhancing resolution and contrast of various dynamic features of the medium being imaged, (2) imaging the dynamic properties of the target medium, and (3) generating images of the dynamic properties using techniques that reduce the need for undue system calibration and produce more stable solutions with the reconstruction algorithm.

It is one object of the invention to generate a map of the dynamic properties of a scattering medium in a cross-sectional view from a time series of collected data measurements. The measurements are obtained by directing energy into the target during a period of time and measuring the energy emerging from the target during the period of time, whereby a time series of measured energy is collected.

It is another aspect of the invention to generate a map of the cross-sectional dynamic properties of the target medium in a cross-sectional view from a time series of images of the cross-sectional properties of the target medium, wherein the dynamic properties are extracted from the time series of images using time series analysis methods.

It is a further aspect of the invention to generate a map of the cross-sectional dynamic properties of the target medium from the time series of measurements at each detector, wherein the dynamic properties are extracted from the time series of measurements at each detector using time series analysis methods.

It is a further aspect of the invention to construct a map of the dynamic properties of the medium, wherein the measured energy is processed using a modified perturbation formulation referred to as the normalized difference method, based on the radiation transport equation, using relative energy measurements. The relative energy measurements being, for example, the relative difference between an instantaneous measure and a time average mean of measures.

BRIEF DESCRIPTION OF THE FIGURES

For a better understanding of the invention, together with the various features and advantages thereof, reference should be made to the following detailed description of the preferred embodiments and to the accompanying drawings wherein.

DETAILED DESCRIPTION OF THE INVENTION

Introduction

Figure 1:
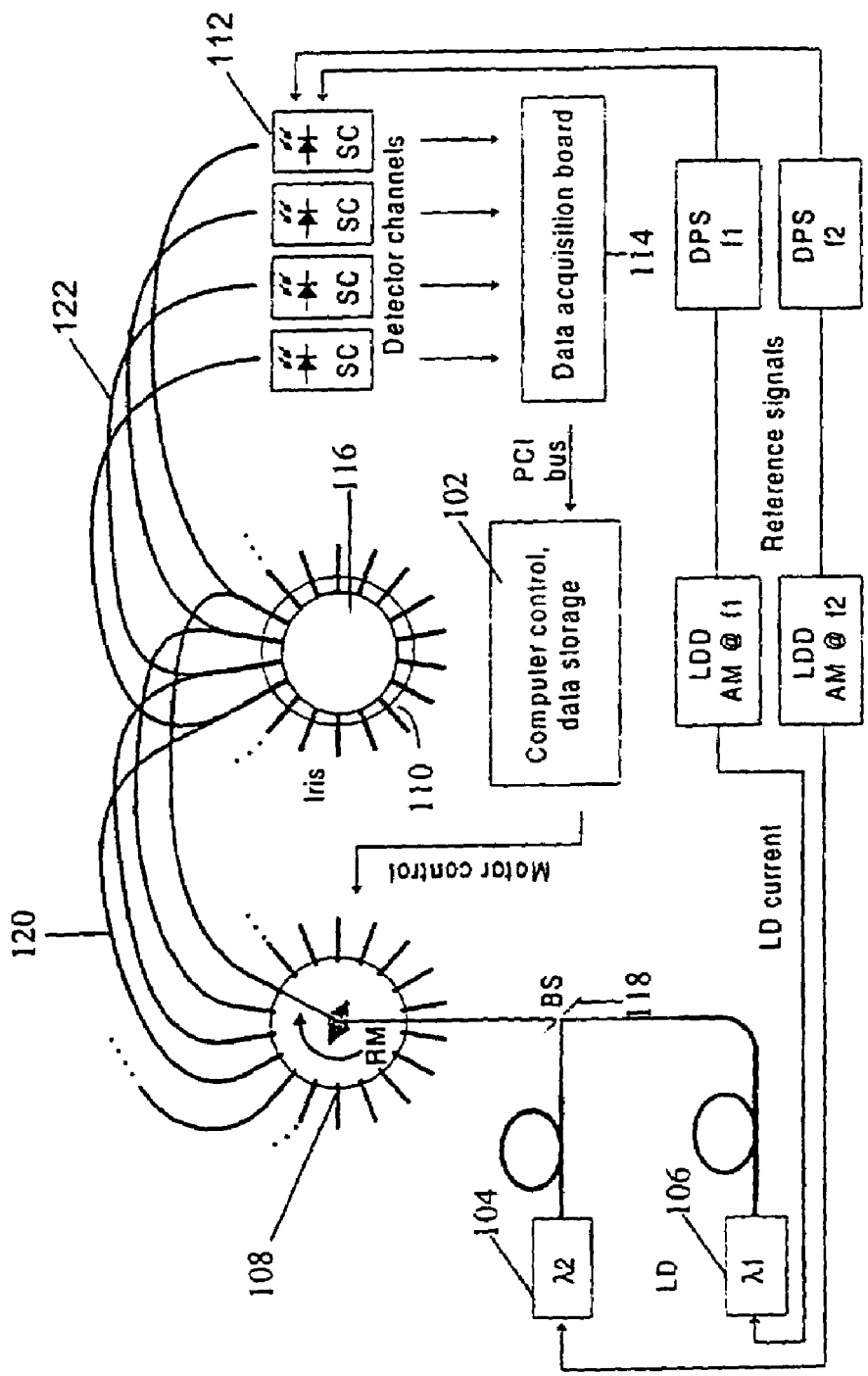
FIG. 1 is a schematic illustration of an exemplary imaging system.

The present invention is built upon known basic approaches to tomographic imaging of a scattering medium, by enabling the investigation of the spatio temporal dynamics of a target medium. This enhancement represents a fundamentally new imaging modality with broad based applications such as in industrial processes involving preparation of powdered mixtures, imaging subsurface turbulence in murky waters and throughout clinical medicine both as a highly sensitive diagnostic imaging tool, as well as for use in treatment planning, therapeutic monitoring and follow-up.

For example, the present invention recognizes that the occurrence of dynamic behavior in human tissue lends the collected data and reconstructed images to evaluation using time series analysis methods, including pattern recognition schemes. Dynamic behavior is known to occur in vascular structures in response to cardiac, respiratory, vasomotor and local metabolic influences. Because optical tomography, based on near infrared measurements is sensitive to hemoglobin, which is nearly always restricted to the vascular compartment time variations in the measured signal, can be used to reveal the vascular frequencies. Although, similar information can be obtained by photoplethysmography, it is not available for large tissue structures nor in an cross-sectional imaging modality.

Detection of these temporal signatures/dynamic behaviors in a cross-sectional view provides a wealth of new information. For instance, the presence (or absence) of a cardiac frequency with respect to known anatomic landmarks (e.g., major arteries) provides a measure of the patency of localized arterial flow. Low-amplitude signals might suggest the presence of arterial stenosis. In addition, it is well appreciated that blood flow is under autonomic control. The absence or attenuation in amplitude of the respiratory or vasomotor frequencies might suggest an underlying peripheral neuropathy.

Further insight concerning the presence or absence of basic control mechanisms can be obtained from time-frequency analysis methods. For instance, the low-frequency vasomotor response in the major arteries of the forearm are nearly synchronous, both ipsilaterally and contralaterally, and under tight autonomic control. Disorganization of this control might suggest the presence of pathology. In fact, loss of control mechanisms is a well known hallmark of neoplastic tissues. The nearly total absence of the vasomotor response in tumor tissue is of particular interest.

Still another factor motivating dynamic measures is an appreciation of the information content available from the study of homeostatic challenges. It is well appreciated that the altered vascular architecture in tumors leads to a condition of sluggish perfusion. The existence of such states maybe be clearly revealed by induction of a homeostatic challenge. This could take on several forms. For example, simple manipulations such as deep breathing, response to cold, or mild venous congestion imposed by inflation of a pressure cuff, all have been shown to produce large amplitude local variations in the optical signals attributable to tissue blood volume in the forearm. Extension of these measures to the breast and other tissue could reveal the presence of tumors with high specificity by virtue of an altered hemodynamic response.

There are other important implications to be considered concerning the value of measuring the time-varying properties of hemoglobin states in a cross-sectional view. For instance, the details of the measured dynamics at the various vascular frequencies need not be the same for measures of blood volume and blood oxygenation. In addition, given the known heterogeneity in tissue perfusion, even in healthy tissue, whatever dynamic features do exist will themselves be spatially varying. Moreover, altered dynamics in blood volume or blood oxygenation indicate altered local metabolic states, the existence of more central control deficits (e.g., autonomic, cardiac, respiratory), or both. Hence these measures can provide an assessment of an integrated physiological state, and also possess important features pertaining to tissue/vascular coupling. In fact, all of the spatiotemporal features attributable to hemoglobin states that do exist will likely respond to a host of pharmacological agents and other treatment modalities. Such measures could serve to identify desired or undesired responses to therapy.

Although these examples relate to the measure of hemoglobin states, it will be appreciated by one skilled in the art that there are a plethora of dynamic features that may be observable using tomographic measures in scattering media in human tissue as well as other scattering media, such as murky water, foggy atmospheres and the like. For instance nerve activation and muscle movement can also by measured owing to changes in scattering properties of tissue. In addition, various exogenous agents that produce contrast in absorption, scatter or fluorescence can be introduced to observe dynamic states of tissue.

The present invention includes new data collection schemes and image analysis methods from which are extracted maps that reveal spatial temporal signatures of the target medium. These methods can include, linear and non-linear time series analysis methods as well as techniques for pattern recognition.

There are three principal elements to practical dynamic imaging. The first element is the use of a fast, parallel, multi-channel acquisition system. For example, a system for use in dynamic optical tomographic imaging of tissue is described briefly below and in further detail in the copending Barbour 4147PC1 application. The second element is to evaluate the acquired tomographic data to produce a cross-sectional image that reveals perturbations of the reconstructed optical coefficients from, for example, a time-averaged mean. This perturbation method is described briefly below and in further detail in the Barbour 4149PC2 application. The third element is to collect a time series of data and subject either the time series of measured data or a time series of reconstructed images from the measure data to analysis. This can include use of various linear and nonlinear time-series analysis methods, and related techniques such as pattern recognition, to extract features identifying dynamic behavior in the properties of the target medium. These methods are discussed in further detail below.

The System

Numerous imaging systems such as those disclosed in the Barbour '355 patent, and the Barbour '322 patent have been developed for use in imaging of a scattering medium which are hereby incorporated by reference.

A system providing high speed data capture of one or more wavelengths simultaneous is disclosed in the Barbour 4147PC1 application. This system is capable of capturing multiple wavelength data at rates up to 150 Hz and enables the reconstruction of cross-sectional images of real-time events associated with vascular reactivity in a variety of tissue structures (e.g., limbs, breast, head and neck). Fast data collection methods are particularly useful because there are many disease states with specific influences on the spatial-dynamic properties of vascular responses in hemoglobin states.

A schematic illustration of an exemplary optical system for fast data collection is shown in FIG. 1. This system includes a computer 102, energy sources 104, 106, a source demultiplexer 108, an imaging head 110, detectors 112 and a data acquisition board 114.

A target 116 placed in the imaging head 110 is exposed to optical energy from sources 104, 106. The optical energy originating from energy sources 104, 106, is combined by beam splitter 118 and is delivered to source demultiplexer 108. The source demultiplexer 108 is controlled by computer 102 to direct the optical energy to source fibers 120 sequentially. Although two energy sources 104, 106 are shown in this embodiment, an additional number of energy sources, each having different wavelengths can be employed. Moreover a single variable wavelength energy source can be implemented such as Ti-Sapphire laser, dye lasers and the like.

Each source fiber 120 carries the optical energy from the demultiplexer 108 to the imaging head 110 where the optical energy is directed into the target 116. The imaging head 110 contains a plurality of source fibers 120 and detector fibers 122 for transmitting and receiving light energy, respectively. Each source fiber 120 forms a source detector pair with each detector fiber 122 in the imaging head 110 to create a plurality of source detector pairs. The optical energy entering the target 116 at one location is scattered and may emerge at any location around the target 116. The emerging optical energy is collected by detector fibers 122 mounted in the imaging head 110.

The detector fibers 122 carry the emerging energy to detectors 112. The detectors 112 measure the energy density of the collected optical energy and generate a corresponding signal. The detectors may comprise any known photodetector such as avalanche photodiodes (APD), silicon PIN photodiodes, silicon photodiodes (SiPD), charged couple devices (CCD), charge inductive device (CID), photomulitplier tubes (PMT), multi-channel plate (MCP) and the like. The energy density is, for situations in which propagating energy is any type of electromagnetic radiation, equivalent to the intensity of said radiation.

The data acquisition board 114 receives the signal, separates it by wavelength, and samples and holds the separated signals for deliver to computer 102. The computer 102 in turn reads and stores the signal for use in image reconstruction and other analysis.

Although the above described systems uses DC measurement techniques with an near infrared energy source, it will be appreciated by those skilled in the art that similar systems can be implemented using other measurement techniques, such as time resolved measurements and frequency domain methods. In addition measures of acoustic signals produced in response to optical absorption (i.e., the photo acoustic effect) as well is use of acoustic sources can be similarly implemented.

Data Collection, Data Analysis and Image Reconstruction In prior methods for imaging of scattering media, measured data was collected for a target medium and an image of the cross-sectional properties of the target was generated based on the measured data. The present invention improves on this basic process by (1) collecting a time series of measured data and (2) analyzing either the raw measured data or a time series of reconstructed images to extract information relating to the dynamics of the target medium.

Data Collection

As discussed above, previously known systems and techniques sought to collect either a time averaged measure thereby minimizing the effect of dynamic behavior or to collect a snapshot of the target. Both of these techniques fail to recognize the value of information contained in the time domain.

The present invention recognizes the value in measuring dynamic properties in highly scattering media and provides methods for collecting and processing the measured data to generate images of dynamic properties. These methods rely on the high speed collection of data using a system such as that described above so that a time series of data sets can be collected in the time domain. The time series analysis techniques, discussed further below, can then be used to extract the dynamic properties of the target from either the measured raw data directly or from a time series of images reconstructed from the measured data.

Data is collected in the present invention using high speed imaging systems such as the system illustrated in FIG. 1. By way of example, referring to FIG. 1, a measured data set is obtained by delivering optical energy to each of the source fibers 120 sequentially and measuring the emerging optical energy at each detector fiber 122 in parallel for each sequential source location. This process is repeated over a period of time so that a time series of data sets are generated, each data set represent a complete set of data (e.g., detector reading for each source position) for reconstruction of a cross-sectional image at an instant in time.

Reconstruction

As discussed above, the time series analysis techniques may be employed prior to image reconstruction (i.e., on the raw measured data) or after image reconstruction (i.e., on the time series of reconstructed images). Where time series analysis methods are applied to raw measured data, image reconstruction will follow based on the processed and extracted dynamic information. For example, one method may compute the discrete Fourier transform of the measured data and then reconstruct images based on the Fourier coefficients at, for instance, a selected frequency.

Of the known reconstruction methods, one group of methods often adopted to analyze the measured data are perturbation methods. Exemplary techniques are disclosed in detail in the Barbour '355 patent and the Barbour 4149PC2 application. Briefly, in model-based techniques a perturbation formulation based on the radiation transport equation, or its approximation the diffusion equation, is generated. The radiation transport equation is a mathematical expression describing the propagation of a particle through a medium from a source location to a detector location as a function of the properties of the medium. The perturbation formulation of this equation relates a perturbation in the measure energy density at a detector to a corresponding perturbation in the properties of the medium.

The standard perturbation equation has the following forms:

$$W \cdot \delta x = \delta I \quad (1)$$

In equation (1), $\delta I$ is a vector of source-detector pair intensity differences between the measured target medium and the known reference medium (i.e., $\delta I = I - I_r$). W is the weight matrix describing the influence that each volume element ("voxel") of the reference medium has on energy traveling from each source to each detector, for all source-detector pairs. The volume elements are formed by dividing a slice of the reference medium into an imaginary grid of contiguous, non-overlapping pieces. Physically, the weight matrix contains the first order partial derivatives of the detector responses with respect to the optical coefficients of each volume element of the reference medium. $\delta x$ is the vector of differences between the known optical properties (e.g., absorption and scattering coefficients) of each volume element of the reference medium and the corresponding unknown optical properties of each volume element of the target medium.

A modification to this standard perturbation equation is presented and disclosed in the Barbour 4149PC2 application. This modified perturbation equation employs relative measurements of energy at the target detectors (e.g., the relative difference between an instantaneous measure and a time averaged mean of measures at a detector). This method improves the stability of the solution to the perturbation equation and reduces sensitivity of the equation to the selected reference medium.

The modified standard perturbation equation replaces $\delta I$ in the standard perturbation equation with a proportionate relative difference between two measured values multiplied by a reference term of the required units as set forth in the equation (2) below:

$$\delta I_r = \left( \frac{I - I_0}{I_0} \right) \cdot I_r \quad (2)$$

In equation (2), $I_r$ is the computed detector reading corresponding to a source-detector pair of a selected reference medium, and $I$ and $I_0$ represent two data measurements for a corresponding source-detector pair on one or more targets (e.g., background vs. target, or time-averaged mean vs. a specific time point, etc.). The resultant term $\delta I_r$ therefore represents a proportionate relative difference between two sets of measured data This modified equation limits the effects of modeling errors and minimize ill-conditioning of the inverse problem while retaining the correct units in the solution.

The corresponding perturbation equation using this modified term is:

$$W_r \cdot \delta x = \delta I_r \quad (3)$$

In equation (3) $W_r$ and $\delta x$ are the same as W and $\delta x$ in equation (1). Referring to equations (2) and (3), it can be seen that in the limit, when $I_r$ equals to $I_0$, this equation reduces to the standard perturbation formulation shown in equation (1). This formulation represents the Born approximation formulation of the modified perturbation equation. A similar expression may be written for the Rytov approximation in the following form:

$$\ln\left(\frac{I}{I_0}\right) = \frac{W_r}{I_r} \delta X \quad (4)$$

The inventive operation performed by equation (2) amounts to a projection procedure by which the information content of a measured proportionate relative data vector is projected onto a selected reference medium. Apart from simplifying measurement requirements, the method represented by equations (3) and (4) also reduces susceptibility of the perturbation equation to boundary and optical property variation between the target and the reference medium. Additionally, iterative solutions of equations (3) and (4) can be easily implemented. In principle, the techniques used in the modified perturbation equation can be used to evaluate any measured proportionate relative quantity to a reference quantity, for example acoustic signals.

Time Series Analysis

As discussed above, time series analysis methods may be applied to either the time series of measurement data or time series of reconstructed images. Applying these methods, the present invention enables investigation of the temporal spatial dynamics of a target medium.

Time series analysis techniques are well-known to provide measures of the frequency structure and time correlation of time varying processes. In addition, hybrid methods such as time frequency analysis (e.g., short time Fourier transform, wavelet analysis) can be used to reveal more complex behaviors in physiological systems such as the known frequency modulation of the cardiac rate upon respiration. Other linear methods can be applied to time domain data such as principle component analysis to reveal the time evolution of specific processes in image maps. Practical examples of these methods as shown in FIGS. 2–19 can be used to identify, in the case of frequency analysis, specific features of the vascular tree, in particular, in the case of imaging human tissue, the major arteries in the forearm. This is possible because of the known structure dependent frequency response of the vasculature (e.g., major arteries beat at a cardiac frequency). Further, time correlation methods may be employed to isolate anatomical landmarks having known phase relationships (e.g., action of antagonistic muscle groups). Additionally, similar procedures can be used on the resultant spatial map to produce the relevant orthogonal information associated with these functions (i.e., maps of the amplitude or phase vs. frequency, correlation vs. time lag, etc.). In addition, complex behaviors in the form of nonlinear chaotic activity is often observable in measures of physiological systems. As is shown in FIGS. 15–19, the described invention is capable of detecting such signatures in a cross-sectional view, in particular as it relates to chaotic behavior of the vasculature as measured by time variations in hemoglobin states. While such behavior has been observed in surface measurements of tissue, with the exception of the instant invention, no other imaging technique is capable of generating equivalent information.

Experimental Validation

The following discussion and some of the above examples presents results validating the methods and advantages of the present inventions. These examples are presented merely as an illustration of the benefits of the present invention and in particular of the ability of dynamic optical tomography to provide high contrast images of time varying features in dense scattering media.

Contrast and Resolution Enhancement

Figure 2A:
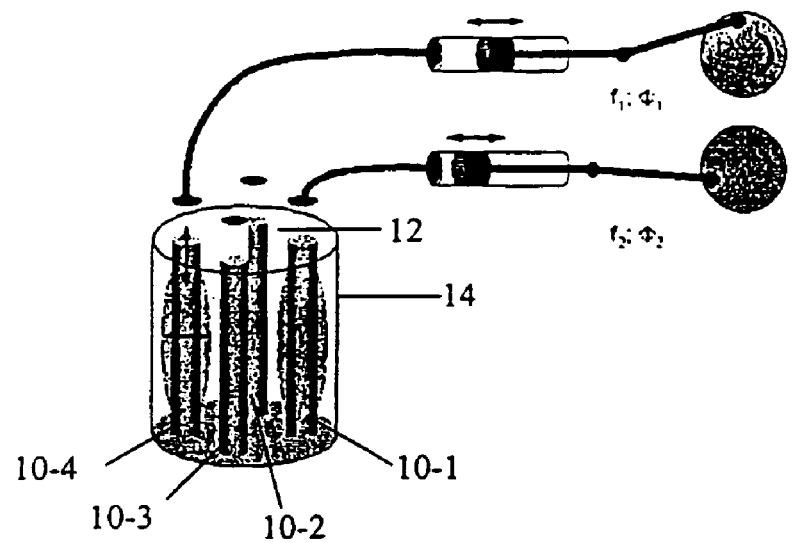
FIG. 2A is an illustration of a mechanism used to rhythmically inflate two balloons.
Figure 2B:
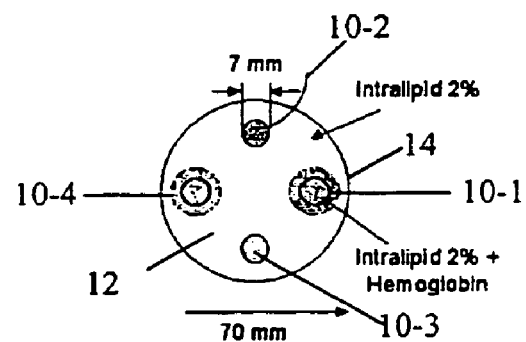
FIG. 2B is a plan view of the illustration of FIG. 2A.
Figure 2C:
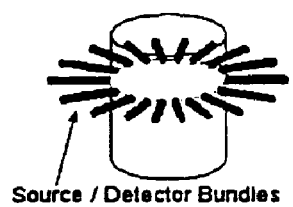
FIG. 2C is an illustration of the geometric arrangement of optical fibers.
Figure 3:
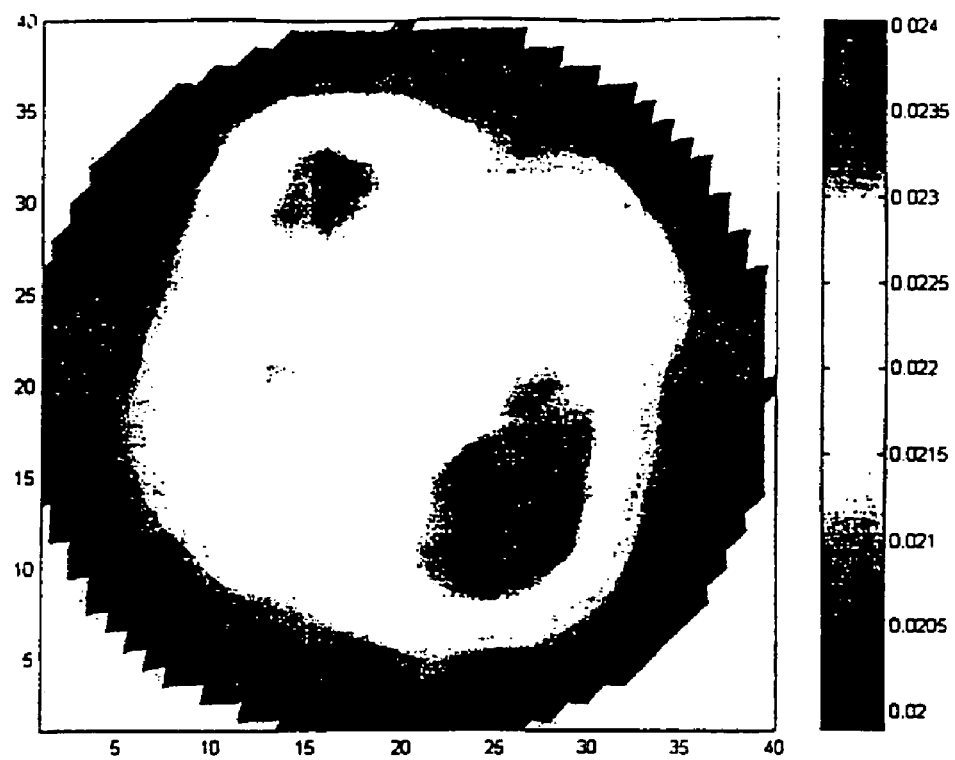
FIG. 3 is a reconstructed image of the cross-sectional properties of a target medium shown in FIG. 2A at an instant in time.
Figure 4:
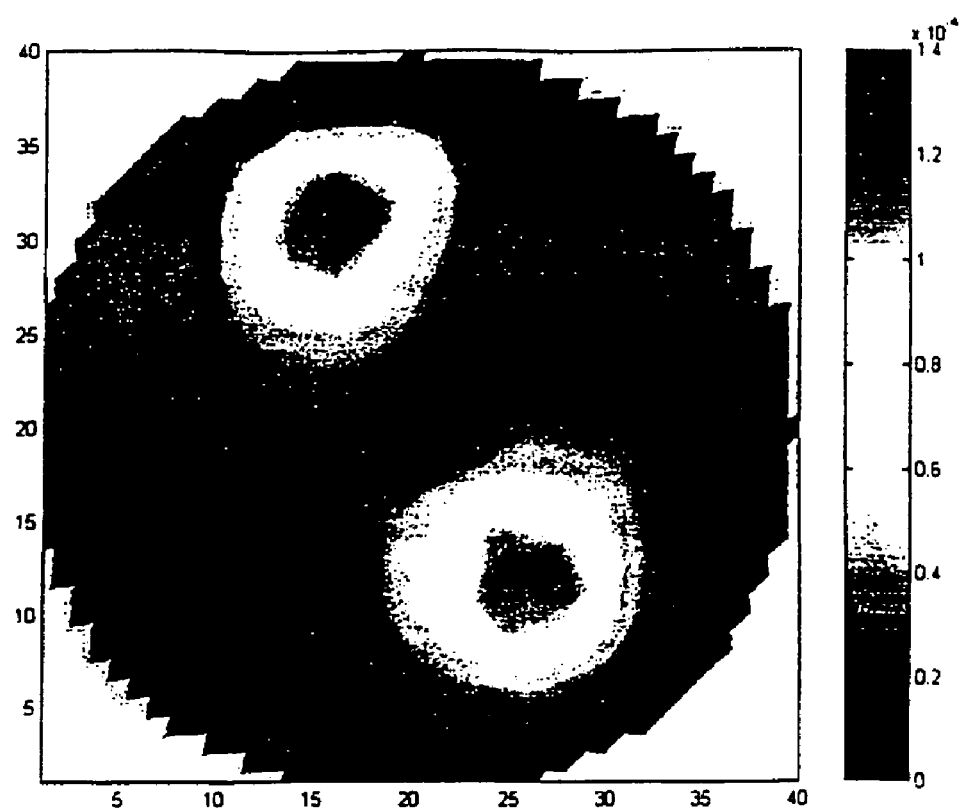
FIG. 4 is a cross-sectional map of the 0.2 Hz component of the amplitude of the image sequence's DFT for the target medium shown in FIG. 2.
Figure 5:
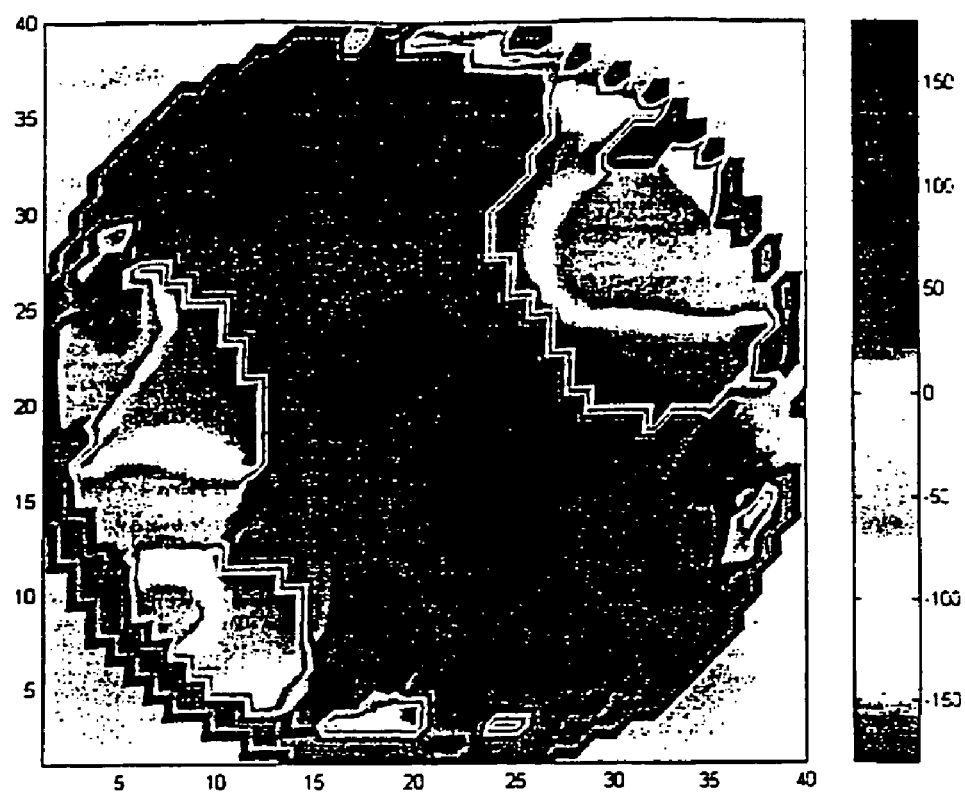
FIG. 5 is a cross-sectional map of the 0.2 Hz component of the phase of the image sequence's DFT for the target medium shown in FIG. 2 with no phase difference between the oscillating balloons.
Figure 6:
FIG. 6 is a cross-sectional map of the 0.2 Hz component of the phase of the image sequence's DFT, 180° phase difference between oscillating balloons.

As disclosed above, application of these time-series analysis methods can extract significantly greater contrast and resolution from the optical imaging data. Image resolution and contrast are important factors for any imaging method. Experience with optical tomography has shown that recovered images have low resolution and contrast. As an example, referring to FIG. 2, tomographic data was collected from a laboratory vessel measuring approximately 8 cm in diameter and containing four balloons 10-1 through 10-3, two of which are static and the other two were modulated at a fixed frequency, with a relative phase of either 0° or 180°. The balloons 10 were suspended in a background scattering medium 12 consisting of 2% (v/v) Intralipid and were filled with a dilute hemoglobin solution (50 $\mu$M). The balloons 10 were arranged in the vessel 14 as shown in FIGS. 2A and 2B. An example of a reconstructed cross-sectional image of absorption obtained at a single time point is shown in FIG. 3. Inspection of FIG. 3 shows that whereas the four objects structure is detectable, the individual balloons are not well resolved, and the recovered contrast is poor. In contrast to this image quality, the map shown in FIG. 4, revealing the discrete Fourier transform (DFT) amplitude at the 0.2 Hz modulation frequency has nearly 100 fold increased contrast. Also evident is that the spatial resolution of the DFT map is considerably improved compared to the maps shown in FIG. 3. The phase portions of the DFT's at 0.2 Hz for the in-phase and the 180°-out-of-phase cases are shown in FIGS. 5 and 6. The phase relations between the two modulated balloons is correctly recovered in each case.

Figure 7A:
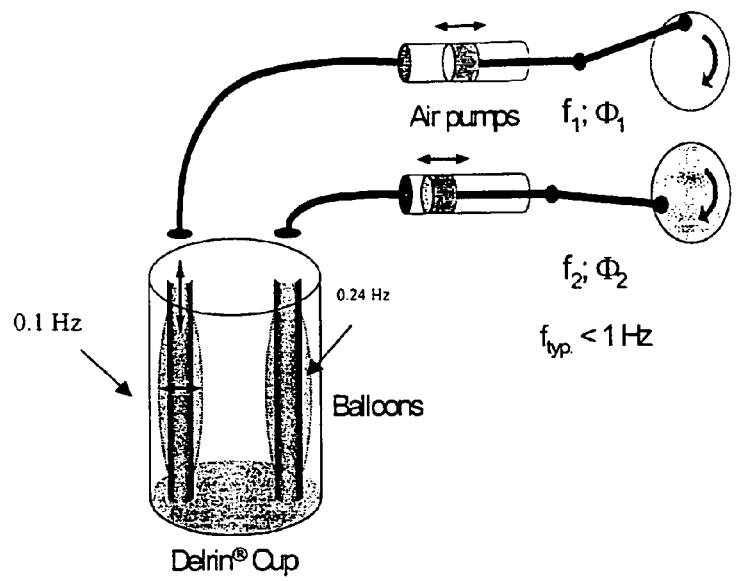
FIG. 7A is a schematic illustration of apparatus with two-balloons.
Figure 7B:
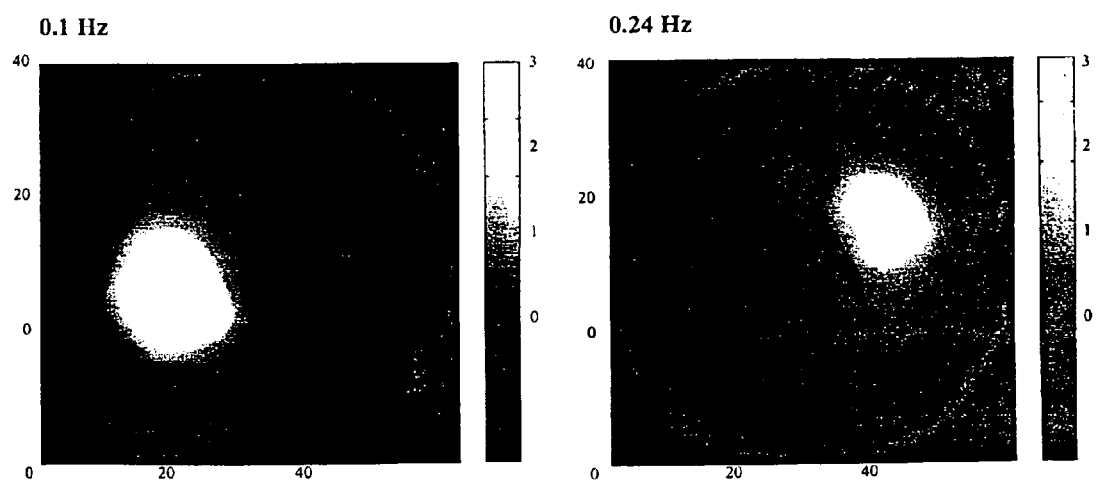
FIG. 7B is a series of reconstructed cross-sectional images from DFT analysis of image time series at 0.1 Hz and 0.24 Hz.

A similar experiment resolving internal structures based on differences in modulation frequency is shown in FIGS. 7A and 7B. In FIG. 7A two balloons were present, one modulated at 0.1 Hz, the other at 0.24 Hz. Inspection of the reconstructed images shown in FIG. 7B, at the corresponding modulation frequencies shows complete spatio-temporal resolution.

Dynamic Physiological Imaging Studies on the Human Forearm

Following a protocol similar to that used to investigate dynamic behavior in the laboratory vessel, the information retrievable from dynamic studies performed on the human forearm at rest and in response to specific provocations are also explored.

Arm at Rest

Figure 8:
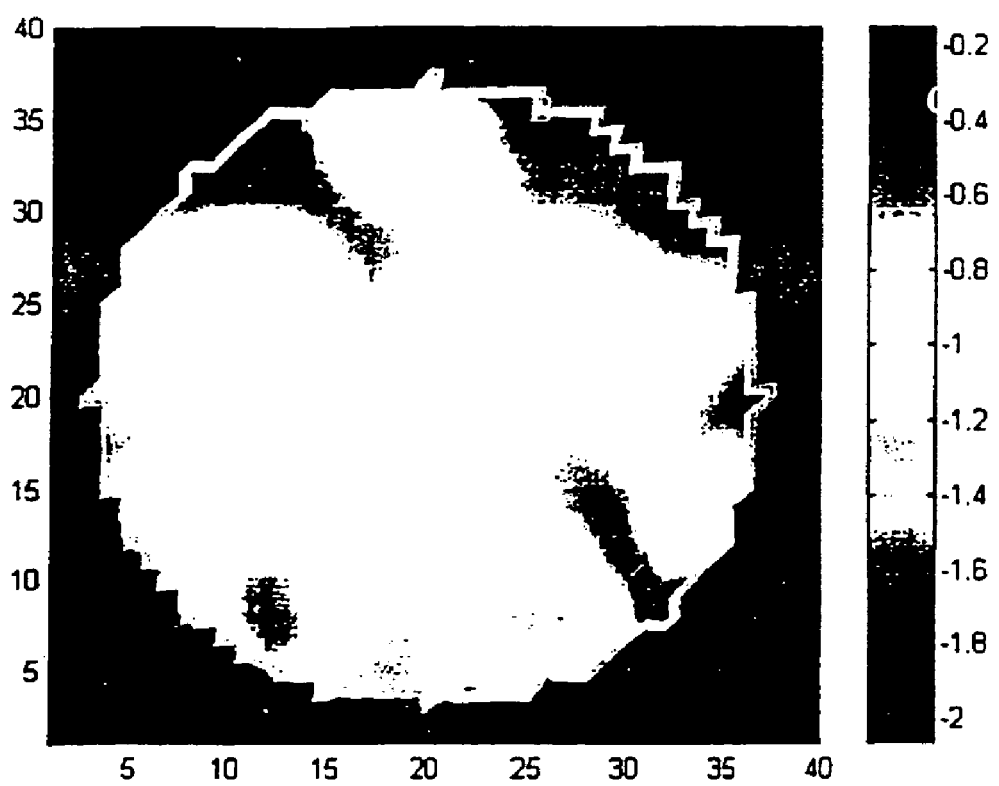
FIG. 8 is a cross-sectional map of ratio of FT amplitude of cardiac to respiratory frequency from forearm study.
Figure 9:
FIG. 9 is an reconstructed MR image of forearm, with identified anatomical structures.
Figure 10:
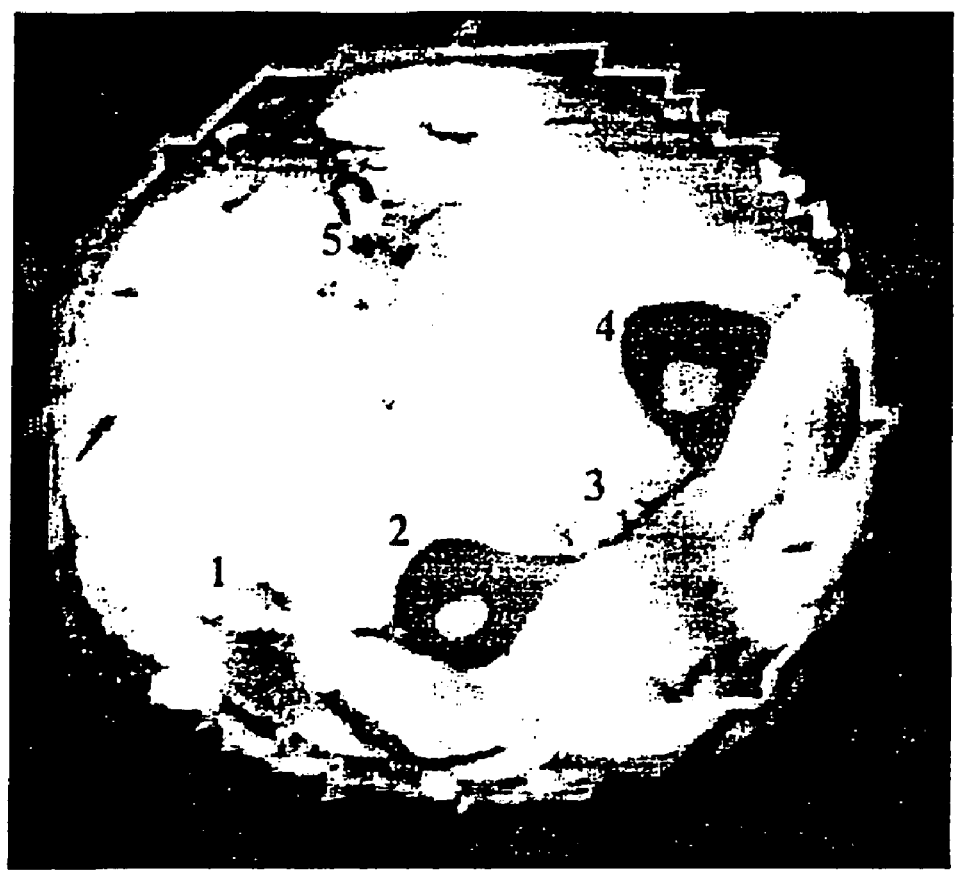
FIG. 10 is an overlay of images shown in FIGS. 8 and 9.
Figure 11A:
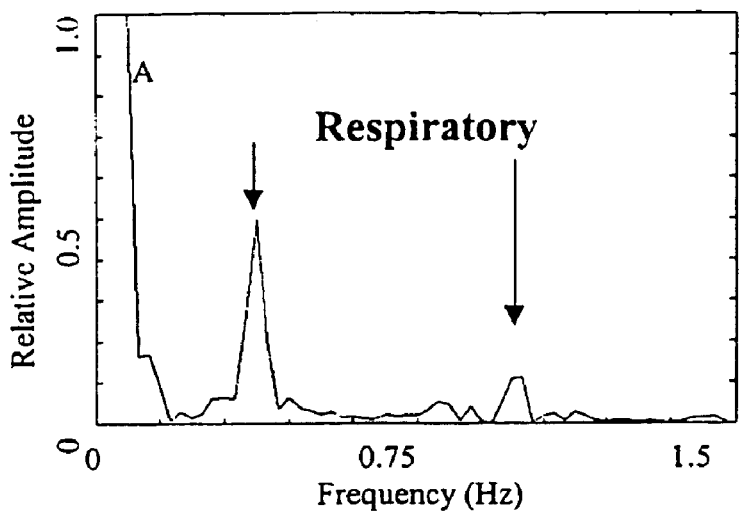
FIG. 11A is a graph of the CSD spectrum amplitude at position (12, 19)
Figure 11B:
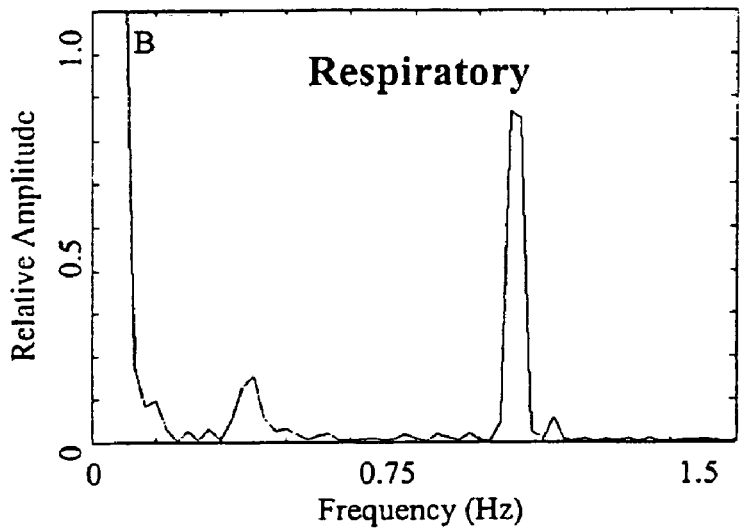
FIG. 11B is a graph of the CSD spectrum amplitude at position (11, 10)
Figure 11C:
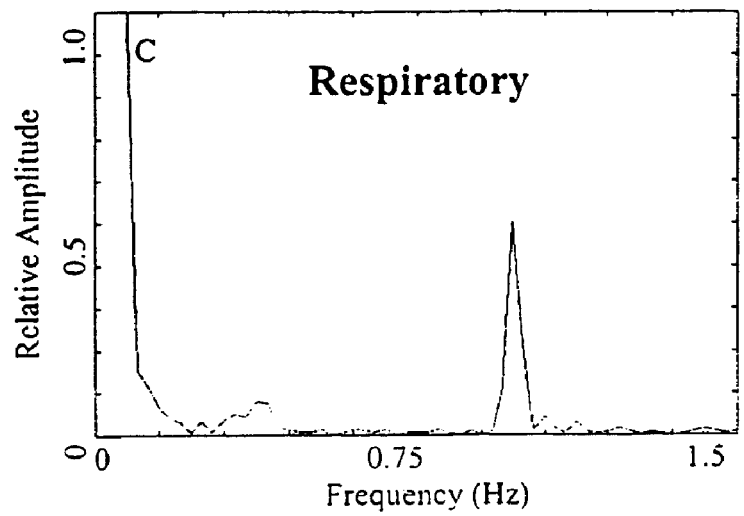
FIG. 11C is a graph of the CSD spectrum amplitude at position (18, 27)

The natural occurrence of vascular frequencies due to respiratory and cardiac activity can be exploited to produce a spatial map revealing the presence of different functional components of the vascular tree. FIG. 8 shows a map of the logarithm of the ratio of the computed DFT amplitudes at the cardiac and respiratory frequencies obtained from a times-series of measurements on the forearm at rest. FIG. 9 is a representative MR image in the same region of the forearm. An overlay of the two maps having the same orientation is shown in FIG. 10. Inspection reveals that in the vicinity of the radial 1, interosseous artery 3 and ulnar artery 5, the ratio of the DFT amplitudes (cardiac to respiratory) is nearly ten times larger than it is in other regions. The radius 2 and ulna 4 are also shown. This response can be seen more clearly in FIGS. 11A–11C, which shows the amplitude of the cross-spectral density (CSD) between a surface detector and specific locations in the image. The particular spectra shown were obtained from points in the image corresponding to locations in the flexor digitorum superficialis muscle, and points near the radial and interosseous arteries. Inspection clearly reveals that in muscle, which contains a dense matrix of microvascular structures, the dominant signal coincides with the respiratory frequency. In contrast, we observe a dominant cardiac frequency in the vicinity of the major arteries. These findings coincide well with the known hemodynamic behavior of the different structures in the vascular tree.

Finger-Flex Study

Figure 12:
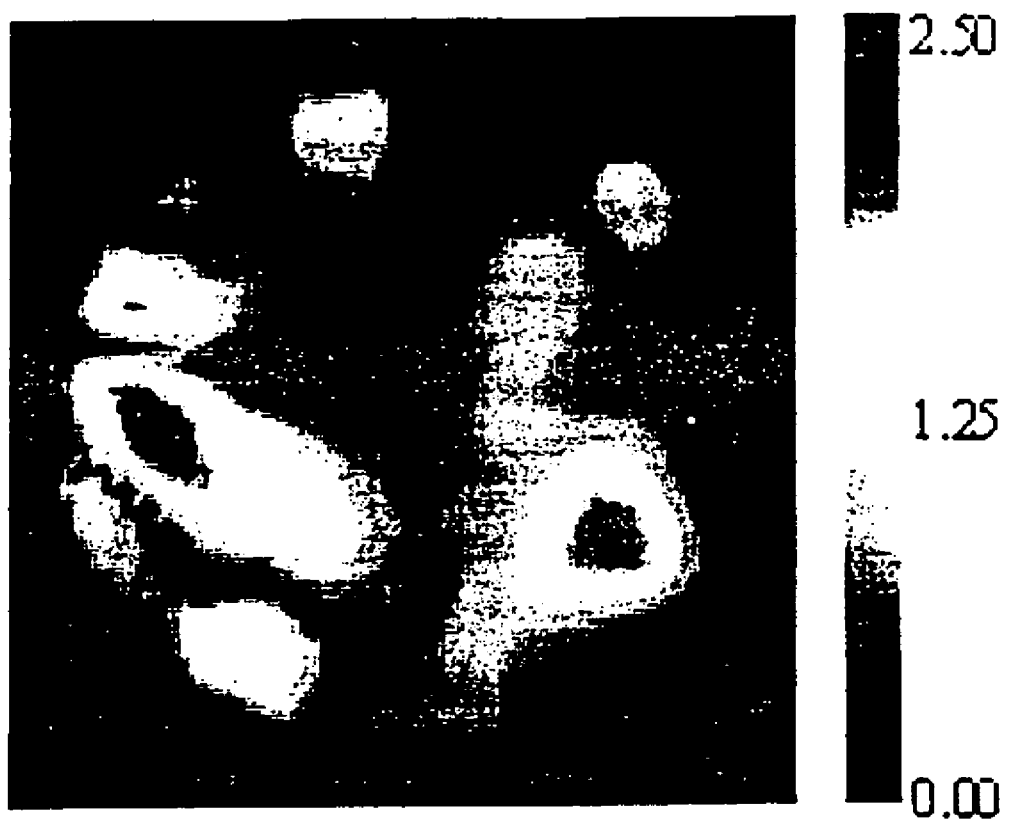
FIG. 12 is a cross-sectional map of amplitude, $\times 10^4$, of the DFT at the finger-flex frequency.
Figure 13:
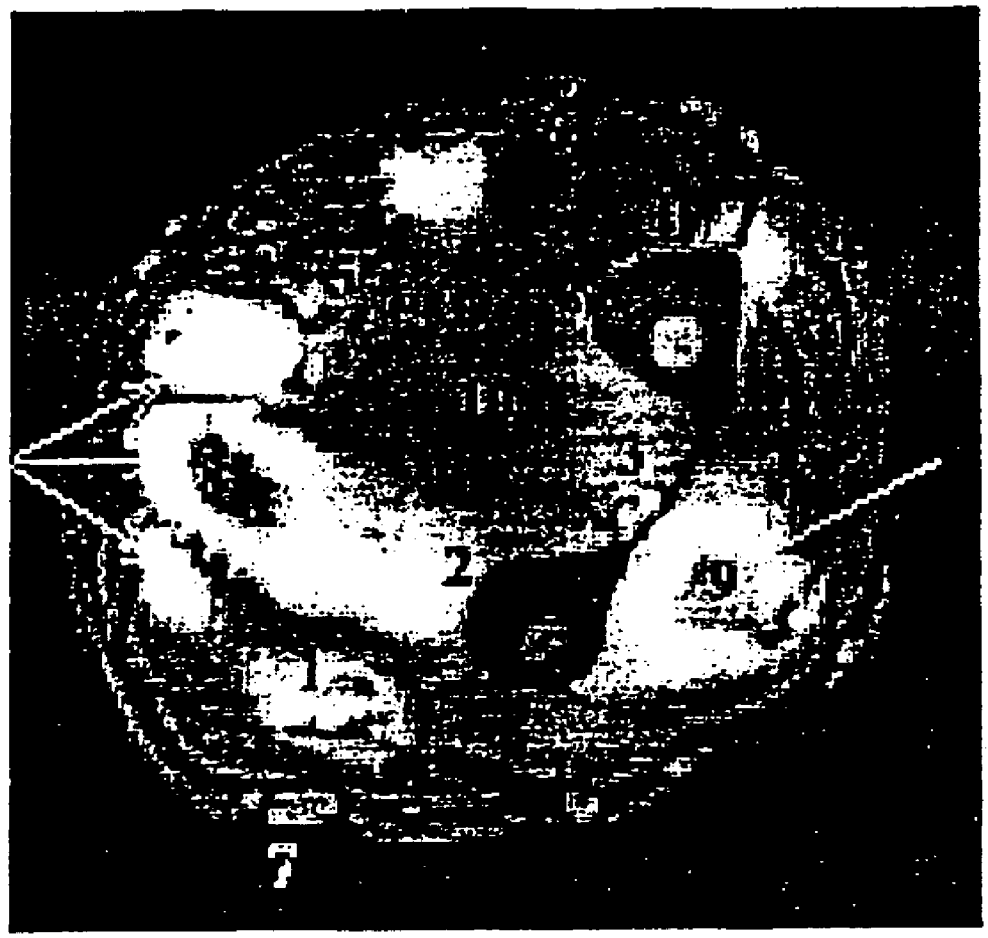
FIG. 13 is an overlay of the map shown in FIG. 12 and an anatomical image (MRI) of the same tissue structures.
Figure 14:
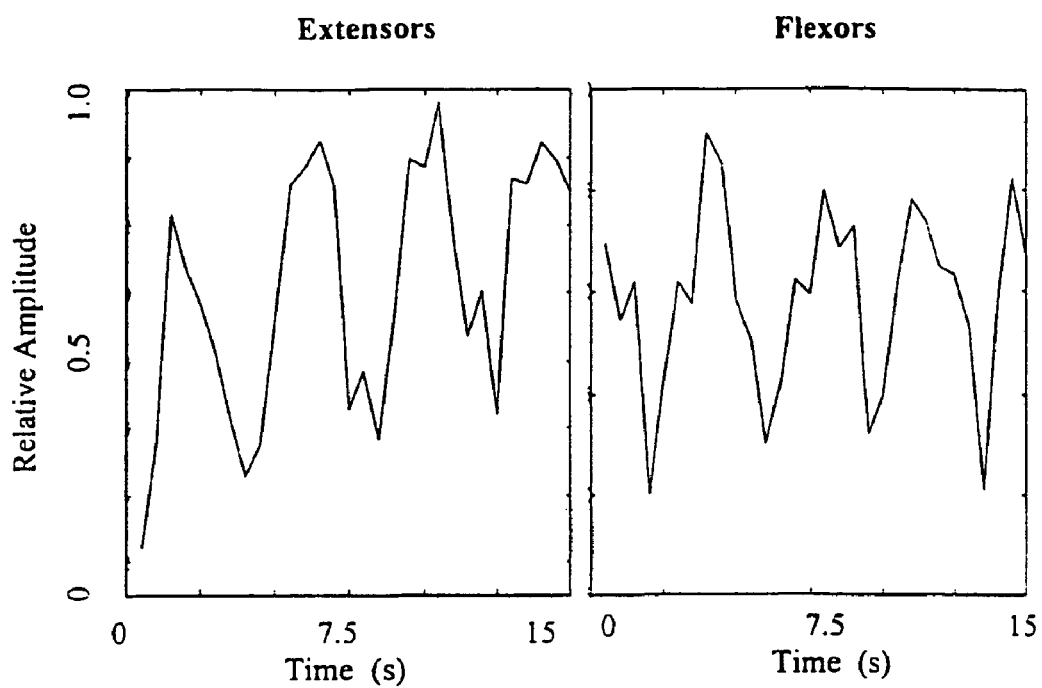
FIG. 14 is a graph of the temporal variations in $\mu_a$ (absorption coefficient) for pixels located within the involved muscle groups.

In this study we explored further our ability to measure dynamic behavior in highly scattering media, such as the human forearm, by examining a time series of images obtained from measurements performed on a subject while conducting a finger-flex exercise. Finger flexing involves the action of so-called antagonistic muscle groups that are located on opposite sides of the forearm, specifically, the flexor digitorium superficialis on the ventral side and the extensor digitorum on the dorsal side. Results shown in FIG. 12 show a map of the amplitude of the DFT at the finger-flexing frequency (~0.25 Hz). FIG. 13 shows an overlay of this image onto an MR image of the same forearm in the same orientation. Inspection reveals that positions of maximum amplitude for finger-flexing coincide well with the two involved muscle groups. Further evidence supporting the accuracy of this assignment is shown in FIG. 14. Plotted are time-series values of recovered absorption values at points in the image coinciding with the involved muscles. Noteworthy is the observation that the two signals are approximately 180° out of phase with each other, which is the expected response from the action of antagonistic muscle groups.

Imaging the Complexity of the Vascular Response

Figure 15:
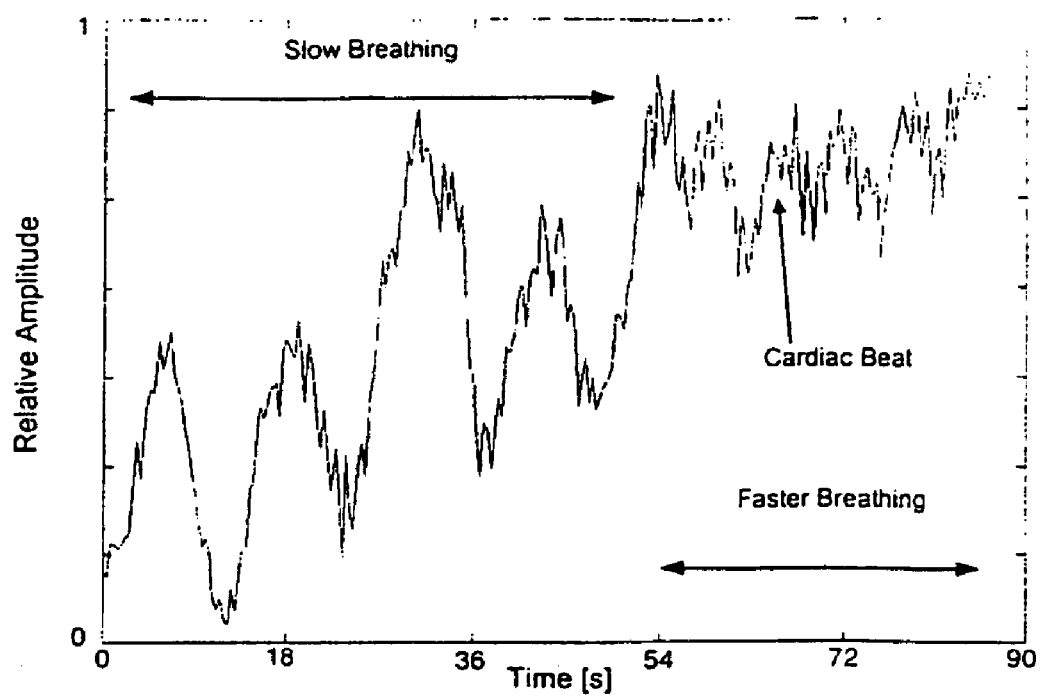
FIG. 15 is a graph of the time-dependent intensity variations for forearm measurements observed for a detector positions opposite the source.

One feature of the disclosed methods that may have considerable practical significance is the potential to obtain reliable estimates of the complexity of the vascular response. The significance of such measures is that they can reveal features of an integrated physiological state that are simply not measurable by using linear methods. Accordingly, in this study we have sought to confirm previous reports in the literature that indicate nonlinear chaotic behavior in vascular rhythms, as has been measured typically by surface laser Doppler methods. Specifically, we have computed certain measures that can reveal nonlinear behavior from time-series image data of the forearm of a subject performing a series of deep-breathing exercises. The influence of a respiratory stimulus was chosen as a simple noninvasive means to amplify the natural oscillatory activity of the vasculature. FIG. 15 shows an example of the magnitude of the signal response caused by deep breathing. The measures we have computed from the pixel data include v, the correlation dimension, and, $\lambda_1$, the largest Lyapunov exponent. Positive values for the latter indicate divergence of trajectories in state space, a finding consistent with a chaotic time series. A value of zero indicates no net divergence and is observed with stochastic data, while negative values indicate system damping.

The computed values displayed in a cross-sectional shown in FIG. 16, below were obtained using the method of Rosenstein et al. (Physica D, 65, 117–134 (1993)) for small data sets. The image series comprised 240 consecutive time points reconstructed from data collected at a rate of 2.8 Hz. The respiration rate was 0.08 Hz for the first 150 time points, and then doubled for the remainder of the measurement period. To assist in timing and repeatability, the volunteer was asked to adjust his respiratory rate to match the beat of a metronome.

Figure 16:
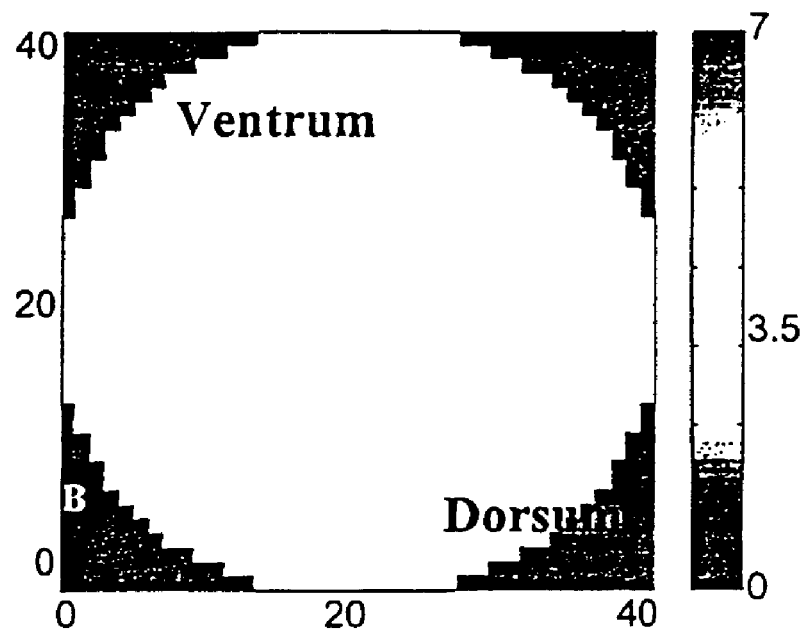
FIG. 16 is a cross-sectional map of the correlation dimension, v, computed, in each pixel, from time series of reconstructed images of $\mu_a$ (810 nm) obtained from representative detector data shown in FIG. 15.
Figure 17:
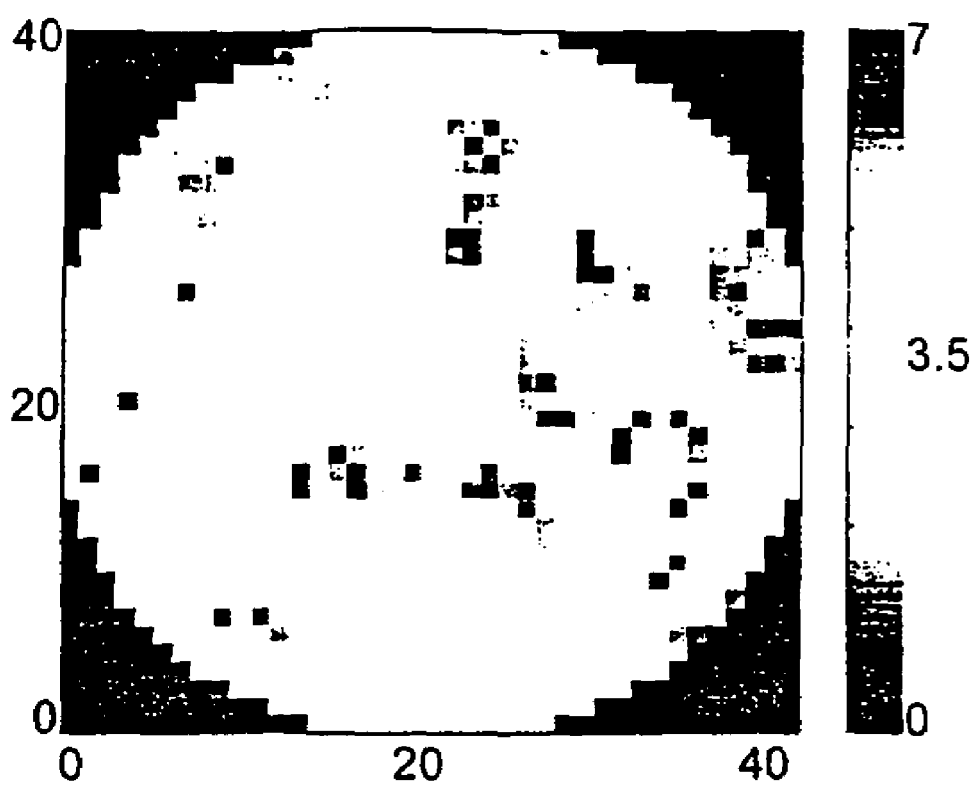
FIG. 17 is a cross-sectional map of the correlation dimension, v, computed in each pixel from time series of reconstructed images of $\mu_a$ (810 nm) obtained from measurements performed on a solid white Delrin® rod.

Referring to FIG. 16, each pixel in the derived image series was band-pass filtered over a range that included the vasomotor and respiratory frequencies (0.05–0.35 Hz). Such filtering colors the noise and can lead to spurious low values for the correlation dimension. For this reason data obtained from a stochastic time series in a similar fashion was treated similarly. The control data set was obtained by computing an image time series from measurements performed on a solid white plastic rod composed of white Delrin®, whose scattering properties are similar to those of tissue. The rod diameter was 9 cm.

As shown in FIG. 16, the range of correlation dimensions computed from the physiological image time series is between 2 and 4 for most pixels. Significantly, these values are in close agreement with previous studies that measured the correlation dimensions of arterial and arteriolar vasomotion in in vitro rat or rabbit preparations. A similar analysis on the rod data, shown in FIG. 17, reveals significantly higher values, a finding consistent with the character of the time series.

Figure 18:
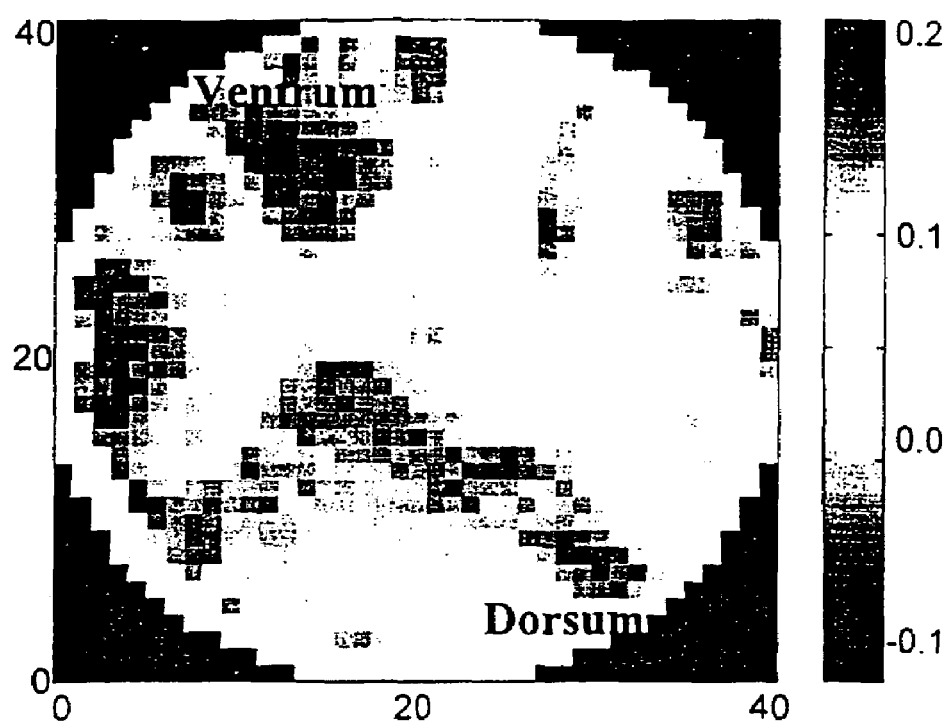
FIG. 18 is a cross-sectional map of $\lambda_1$ (largest value of Lyapunov exponent) in each pixel derived from the same time series of reconstructed $\mu_a$ (810 nm) images as used to generate v map shown in FIG. 16.
Figure 19:
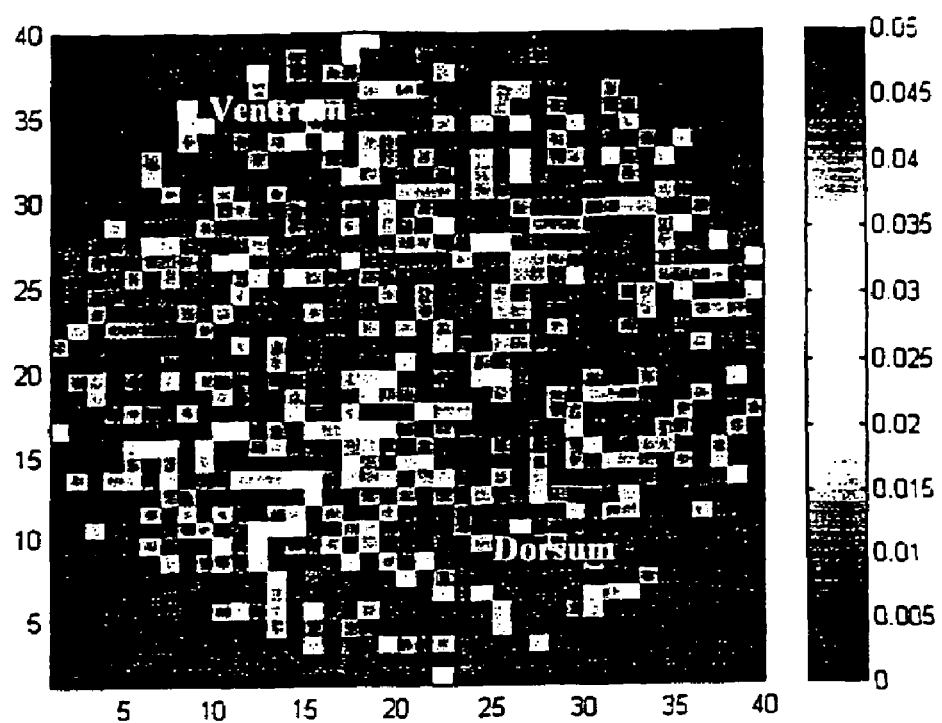
FIG. 19 is a cross-sectional comparison map of the $\lambda_1$ map in FIG. 18 to corresponding results obtained from surrogate data sets.

The image in FIG. 18 shows a spatial map of $\lambda_1$ computed for each pixel. Because a stochastic time series can also yield positive values for $\lambda_1$, we have computed surrogate data sets for each pixel and performed a test for statistical significance. Surrogate data were computed by randomizing the phase of the Fourier spectrum followed by recovery of the resultant time series from which the surrogate $\lambda_1$ were computed. FIG. 19 shows a map of the significance level, in each pixel, for the physiological data compared to surrogate data. Inspection reveals that most areas of the map have positive $\lambda_1$ values that fail the null hypothesis. Note that the optical measures performed are known to exhibit considerable sensitivity to the microvessels. These findings, indicating the occurrence of nonlinear chaotic activity of the vasculature revealed in a cross-sectional view, thus coincide well with previous reports whose measures were limited to the study of vascular dynamics in the near surface of tissue. Its worth emphasizing that the above findings are the first of their kind and, to the best of our knowledge, no other imaging modality is capable of providing equivalent measures of vascular dynamics.

Strategies of the types explored can be used to investigate a range of vascular anomalies. For example, the deep breathing exercise may aid in the diagnosis of cancer. Solid tumors have altered vascular beds. Enhanced breathing will cause redistribution of the flow patterns in tissue. Regions having altered vascular architecture should behave very different from those with a normal architecture. A similar approach can be used to identify tissue regions "at risk" due to the effects of diabetes, atheroscleorsis (small vessel disease), or long term effects of smoking (large vessel disease).

Although the examples above focus on near infrared energy sources for imaging human tissue, the methodology of the present invention is applicable to essentially any wavelength for any energy source (e.g., electromagnetic, acoustic, etc.), responsive to dynamic properties of a scattering medium and for any source condition (e.g., time independent, time harmonic, time resolved). Moreover, although the examples above investigate cross-sectional imaging, it will be appreciated that these methods are applicable to and include volumetric measures and imaging.

Further, although illustrative embodiments have been described herein in detail, those skilled in the art will appreciate that variations may be made without departing from the spirit and scope of this invention. Moreover, unless otherwise specifically stated, the terms and expressions used herein are terms of description and not terms of limitation, and are not intended to exclude any equivalents of the system and methods set forth in the following claims.

What is claimed is:

1. A method for enhanced imaging of a target medium comprising:
   using optical tomography to direct energy into a target medium from at least one source during a period of time, the target medium having dynamic properties during the period of time;
   wherein the energy from the at least one source is highly scattered by the target medium and emerges from the target medium at different locations around the target medium;
   measuring the energy emerging from the target medium during the period of time using a plurality of detectors positioned to detect the emerging energy at the different locations;
   the energy emerging from the target medium at the different locations being a function of the dynamic properties of the target medium; and
   generating a map of the dynamic properties of the target medium based on the measured energy emerging from the target medium at the different locations.

2. The method of claim 1, further comprising:
   generating a time series of images of the properties of the target medium based on the measured energy emerging from the target medium, wherein each image represents the cross-sectional properties of the target medium at a time interval during the period of time.

3. The method of claim 2, wherein generating the map of the dynamic properties of the target medium comprises processing the time series of images using time series analysis methods.

4. The method of claim 1, wherein generating the map of the dynamic properties of the target medium comprises processing the measured energy at each of the plurality of detectors using time series analysis methods.

5. The method of claim 1, wherein the map of the dynamic properties is generated using time series analysis methods that comprise linear time series methods.

6. The method of claim 5, wherein the linear time series analysis methods are at least one of frequency analysis, time correlation analysis, time frequency analysis and principle component analysis.

7. The method of claim 1, further comprising applying a provocation to the target medium.

8. The method of claim 7, wherein the target medium comprises human tissue having a vascular tree and the provocation has a dynamic effect on the vascular tree.

9. The method of claim 8, wherein the provocation comprises an autonomic stimulus.

10. The method of claim 8, wherein the provocation comprises a local stimulus.

11. The method of claim 1, wherein the energy comprises optical energy having a wavelength in the near infrared region of the electromagnetic spectrum.

12. The method of claim 11, wherein the optical energy directed toward the medium includes at least two wavelengths of near infrared energy.

13. The method of claim 11, wherein the target medium comprises human tissue having a vascular tree containing blood, the vascular tree comprising veins, arteries and micro vessels, the blood having time varying absorption and scattering properties to the near infrared energy as a function of blood oxygenation and blood volume.

14. The method of claim 13, wherein generating a map of the dynamic properties of the target medium comprises generating an image of at least one of the time varying absorption and scattering properties of the target medium.

15. The method of claim 13, wherein generating a map of the dynamic properties of the target medium further comprises using time series analysis to enhance the contrast of at least one of veins, arteries and micro vessels.

16. The method of claim 1, wherein the energy comprises optical energy in the visible spectrum.

17. A system for enhanced imaging of a target medium, comprising:
   a source for using optical tomography to direct energy into a target medium from at least one source during a period of time, the target medium having dynamic properties during the period of time;
   wherein the energy from the at least one source is highly scattered by the target medium and emerges from the target medium at different locations around the target medium;
   a plurality of detectors positioned at the different locations for measuring the energy emerging from the different locations of the target medium during the period of time, the energy emerging from the target medium at the different locations being a function of the dynamic properties of the target medium;
   a data acquisition means for receiving the measured energy during the period of time; and
   a computer responsive to the data acquisition means, the computer having code for generating a map of the dynamic properties of the target medium based on the measured energy emerging from the target medium at the different locations.

18. The system of claim 17, wherein the computer further includes code for generating a time series of images of the properties of the target medium based on the measured energy emerging from the target medium, wherein each image represents the cross-sectional properties of the target medium at a time interval during the period of time.

19. The system of claim 18, wherein the computer further includes code for processing the time series of images using time series analysis methods to generate the map of the dynamic properties.

20. The system of claim 19, wherein the computer further includes code for processing the measured energy at each detector using time series analysis methods to generate the map of the dynamic properties of the medium.

21. A method for enhanced imaging of a target medium comprising:
   directing energy into a target medium from at least one source during a period of time, the target medium having dynamic properties during the period of time;
   measuring the energy emerging from the target medium during the period of time using at least one detector, the energy emerging from the target medium being a function of the dynamic properties of the target medium; and
   generating a map of the dynamic properties of the target medium based on the measured energy emerging from the target medium, and using nonlinear time series analysis methods.

22. A method for enhanced imaging of a target medium comprising:
   directing energy into a target medium from at least one source during a period of time, the target medium having dynamic properties during the period of time;
   measuring the energy emerging from the target medium during the period of time using at least one detector, the energy emerging from the target medium being a function of the dynamic properties of the target medium; and
   generating a map of the dynamic properties of the target medium based on the measured energy emerging from the target medium;
   wherein the energy is measured by a plurality of measurements collected at a sampling rate not less than twice the reciprocal of the highest frequency of a dynamic property to be imaged.

23. A method for enhanced imaging of a target medium comprising:
   directing energy into a target medium from at least one source during a period of time, the target medium having dynamic properties during the period of time;
   measuring the energy emerging from the target medium during the period of time using at least one detector, the energy emerging from the target medium being a function of the dynamic properties of the target medium; and
   generating a map of the dynamic properties of the target medium based on the measured energy emerging from the target medium; wherein:
   the measured energy is processed using a modified perturbation formulation of a radiation transport equation; and
   the modified perturbation formulation uses relative energy measurements.

24. The method of claim 23, wherein the relative energy measurements are the relative differences between a measure at an instant in time and a time average mean of measures during the period of time.

* * * * *